(12) United States Patent
Rich et al.

(10) Patent No.: US 8,149,402 B2
(45) Date of Patent: Apr. 3, 2012

(54) OPTICAL SYSTEM FOR A FLOW CYTOMETER

(75) Inventors: Collin A. Rich, Ypsilanti, MI (US);
Richard L. Fisher, Ann Arbor, MI (US);
Nathaniel C. Bair, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 350 days.

(21) Appl. No.: 12/197,192

(22) Filed: Aug. 22, 2008

(65) Prior Publication Data
US 2009/0201501 A1  Aug. 13, 2009

Related U.S. Application Data

(63) Continuation-in-part of application No. PCT/US2007/004836, filed on Feb. 22, 2007.

(60) Provisional application No. 61/014,382, filed on Dec. 17, 2007, provisional application No. 61/014,425, filed on Dec. 17, 2007, provisional application No. 61/018,233, filed on Dec. 31, 2007, provisional application No. 60/776,125, filed on Feb. 22, 2006.

(51) Int. Cl.
*G01N 21/00* (2006.01)

(52) U.S. Cl. .......... 356/343; 356/311; 356/338; 422/67; 422/82.08; 436/36; 436/50; 436/164

(58) Field of Classification Search ................... 356/343, 356/338, 311, 318; 436/36, 50, 55, 164, 436/172; 422/73, 67, 82.08, 82.05
See application file for complete search history.

(56) References Cited

U.S. PATENT DOCUMENTS

| | | | |
|---|---|---|---|
| 4,826,660 A | 5/1989 | Smith | |
| 4,933,813 A * | 6/1990 | Berger | 362/2 |
| 5,028,127 A | 7/1991 | Spitzberg | |
| 5,139,609 A | 8/1992 | Fields et al. | |
| 5,367,474 A | 11/1994 | Auer | |
| 5,739,902 A | 4/1998 | Gjelsnes et al. | |
| 5,798,222 A | 8/1998 | Goix | |
| 5,920,388 A | 7/1999 | Sandberg et al. | |
| 6,016,376 A | 1/2000 | Ghaemi et al. | |
| 6,067,157 A * | 5/2000 | Altendorf | 356/338 |
| 6,091,502 A | 7/2000 | Weigl et al. | |
| 6,097,485 A | 8/2000 | Lievan | |
| 6,154,276 A | 11/2000 | Mariella, Jr. | |

(Continued)

FOREIGN PATENT DOCUMENTS

EP  1396736  3/2004

(Continued)

*Primary Examiner* — Gregory J Toatley
*Assistant Examiner* — Iyabo S Alli
(74) *Attorney, Agent, or Firm* — Jeffrey Schox

(57) ABSTRACT

The preferred embodiments of the invention is an optical system for a flow cytometer including a flow channel with an interrogation zone, and an illumination source that impinges the flow channel in the interrogation zone from a particular direction. The optical system preferably includes a lens system and a detection system. The lens system preferably includes multiple lens surfaces arranged around the flow channel and adapted to collect and collimate light from the interrogation zone. The detection system preferably includes multiple detectors adapted to detect light from the lens system. Each detector preferably includes a local filter that independently filters for specific wavelengths. Thus, the user may easily swap the filters in any order to achieve the same detection parameters.

43 Claims, 6 Drawing Sheets

U.S. PATENT DOCUMENTS

| | | |
|---|---|---|
| 6,377,721 B1 | 4/2002 | Walt et al. |
| 6,403,378 B1 | 6/2002 | Phi-Wilson et al. |
| 6,469,787 B1 | 10/2002 | Meyer et al. |
| 6,519,355 B2 | 2/2003 | Nelson |
| 6,522,775 B2 | 2/2003 | Nelson |
| 6,636,623 B2 | 10/2003 | Nelson et al. |
| 6,700,130 B2 | 3/2004 | Fritz |
| 6,710,871 B1 | 3/2004 | Goix |
| 6,816,257 B2 | 11/2004 | Goix |
| 6,859,570 B2 | 2/2005 | Walt et al. |
| 6,869,569 B2 | 3/2005 | Kramer |
| 6,897,954 B2 | 5/2005 | Bishop |
| 6,936,828 B2 | 8/2005 | Saccomanno |
| 6,944,322 B2 | 9/2005 | Johnson et al. |
| 7,009,189 B2 | 3/2006 | Saccomanno |
| 7,012,689 B2 | 3/2006 | Sharpe |
| 7,075,647 B2 | 7/2006 | Christodoulou |
| 7,106,442 B2 | 9/2006 | Silcott |
| 7,113,266 B1 | 9/2006 | Wells |
| 7,232,687 B2 | 6/2007 | Lary et al. |
| 7,262,838 B2 | 8/2007 | Fritz |
| 7,362,432 B2 | 4/2008 | Roth |
| 2002/0028434 A1 | 3/2002 | Goix |
| 2003/0048539 A1 | 3/2003 | Oostman, Jr. et al. |
| 2004/0048362 A1 | 3/2004 | Trulson et al. |
| 2004/0175837 A1 | 9/2004 | Bonne et al. |
| 2004/0201845 A1 | 10/2004 | Quist et al. |
| 2005/0047292 A1 | 3/2005 | Park et al. |
| 2005/0057749 A1 | 3/2005 | Dietz et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2006/0002634 A1 | 1/2006 | Riley |
| 2006/0023219 A1 | 2/2006 | Myer et al. |
| 2006/0281143 A1 | 12/2006 | Liu et al. |
| 2007/0041013 A1 | 2/2007 | Fritz |
| 2007/0096039 A1 | 5/2007 | Kapoor et al. |
| 2008/0064113 A1 * | 3/2008 | Goix et al. ............... 436/86 |
| 2009/0174881 A1 | 7/2009 | Rich |

FOREIGN PATENT DOCUMENTS

| | | |
|---|---|---|
| JP | 04-086546 H | 3/1992 |
| JP | 10-227737 H | 8/1998 |
| WO | 2005/073694 | 1/2005 |
| WO | WO/2005/017499 | 2/2005 |
| WO | WO/2005/073694 | 8/2005 |
| WO | WO 2007/100723 | 2/2007 |
| WO | WO 2008/058217 | 11/2007 |

* cited by examiner

- - - - WAVELENGTH 1
——— WAVELENGTH 2

DIRECTION OF
LIGHT TRAVEL ←

OPTICAL SYSTEM FOR A FLOW CYTOMETER

CROSS-REFERENCE TO RELATED APPLICATIONS

This application is a continuation in part of international application number PCT/US07/04836 filed 22 Feb. 2007 and entitled "Optical System for a Flow Cytometer," which claims priority to U.S. Provisional Application No. 60/776,125, filed 22 Feb. 2006.

This application also claims the benefit of U.S. Provisional Application No. 61/014,382, filed 17 Dec. 2007 and entitled "Optical System for a Flow Cytometer," U.S. Provisional Application No. 61/014,425, filed 17 Dec. 2007 and entitled "Optical System for a Flow Cytometer," U.S. Provisional Application No. 61/018,233, filed 31 Dec. 2007 and entitled "Optical System for a Flow Cytometer." All five patent documents (one international patent application and the four US Provisional Applications) are incorporated in their entirety by this reference.

TECHNICAL FIELD

This invention relates generally to the flow cytometer field, and more specifically to a new and useful optical system in the flow cytometry field.

BACKGROUND

The conventional optical system for flow cytometers includes a collecting lens to collect light from the interrogation zone, beam splitters to split the light into different channels based on wavelength, and several detector subsystems with filters to pass only particular wavelengths (such as 515-545 nm, 564-606 nm, and 653-669 nm).

To use the conventional optical system, the beam splitters and filters must be arranged in a very particular order (monotonically increasing or decreasing order). For example, a first beam splitter must split between the two lower frequency bands, a first detector subsystem must filter between the lowest frequency band, a second beam splitter must split between the two higher frequency bands, a second detector subsystem must filter between the middle frequency bands, and a third detector subsystem must filter between the highest frequency bands. To change the wavelength detection of the conventional optical system (for example, to replace the frequency band that is originally the highest with a frequency band that is now the lowest) would require the re-arrangement of the entire optical system (including swapping both filters and beam splitters). In other words, with a conventional optical system, the step of filtering the light of the first channel affects the light of the second channel.

Thus, the user must skillfully arrange the filters in a particular order or the detector subsystems will not function correctly. This limitation prevents the easy swapability of the filters and the easy modification of detection parameters. Further, the particular arrangement of the optical table decreases the reliability and the ruggedness of the flow cytometer since the alignment of the beam splitters affects the detection of each of the detector subsystems.

Thus, there is a need in the flow cytometer field to create a new and useful optical system. This invention provides such new and useful optical system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. The Optical System

Figure 1:
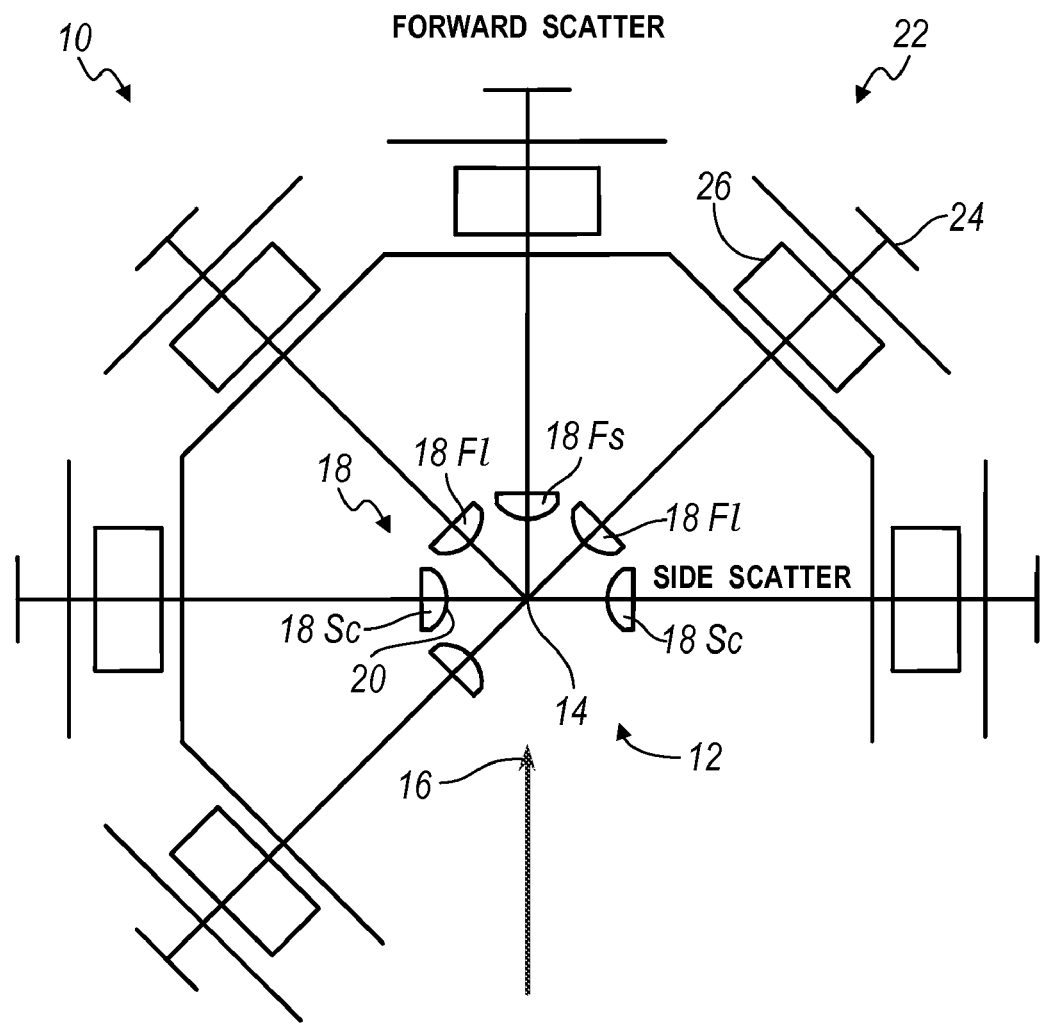
FIG. 1 is a schematic representation of the preferred embodiment of the invention.

As shown in FIG. 1, the optical system 10 of the preferred embodiments of the invention is preferably integrated into a flow cytometer. In this preferred environment, the flow cytometer defines a flow channel 14 with an interrogation zone 12 and includes an illumination source 16 that impinges the interrogation zone 12 from a particular direction. The optical system 10 preferably includes a lens system 18 with multiple lens surfaces 20 arranged around the interrogation zone 12, and a detection system 22 with multiple detectors 24 arranged to detect the light collected and collimated by the lens system 18. The multiple detectors 24 are each coupled to a local filter 26 that independently filters the collected light for specific wavelengths. Although the optical system 10 of the preferred embodiment has been specifically designed for an interrogation zone 12 of a flow cytometer, the system may alternatively be used in any suitable system to collect light along multiple paths from a single point.

The lens system 18 of the preferred embodiment functions to collect and collimate the scattered and/or emitted light from the interrogation zone 12. Preferably, the lens system 18 includes at least three lens surfaces 20 (one forward scatter, one side scatter, and one florescence). More preferably, the lens system 18 includes five or more lens surfaces 20 (one forward, two side scatter, and two or more florescence). In the preferred version, the lens system 18 is composed of separate lenses. In an alternative version, the lens system 18 may be formed as a unitary piece with multiple facets. The lens system 18 is preferably arranged along a plane parallel to the light source and perpendicular to the flow channel 14, but—as discussed in Section Two—may alternatively be arranged in any suitable manner.

Figure 2:
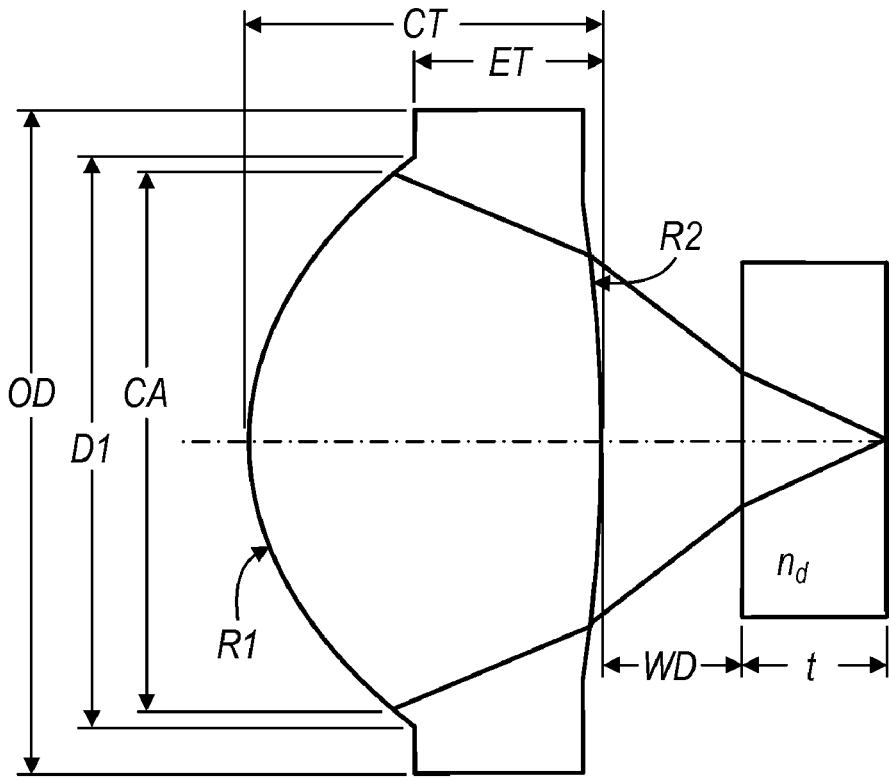
FIGS. 2 and 3 are detailed side and front views, respectively, of a collecting lens of a variation of the preferred embodiment.
Figure 3:
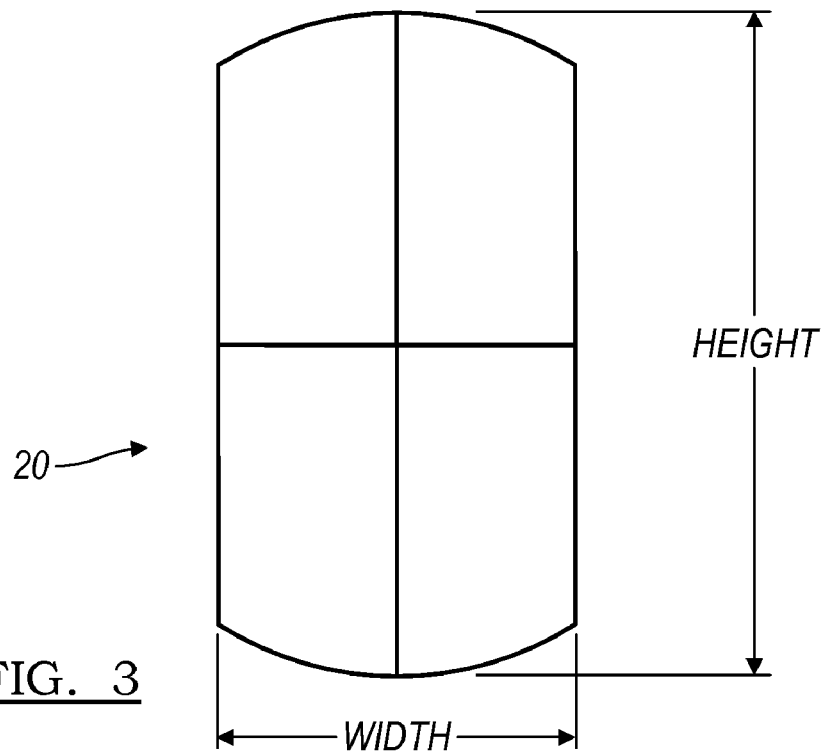

In a first variation, as shown in FIG. 1, the lens system 18 includes at least three whole lenses (preferably a 011-0330 spherical lens sourced from Optosigma of Santa Ana, Calif.). The whole lenses preferably include a usable numerical aperture of approximately 0.31. In a second variation, as shown in FIG. 2, the lens system 18 includes at least three truncated lenses (preferably a 46-347 aspherical lens sourced from Edmund Optics of Barrington, N.J.). In other variations, the lenses may be whole or truncated, may be spherical or aspherical, and may be similar or dissimilar to each other. The truncation of the lenses functions to increase the light collecting ability of the lens system 18, while maintaining a close proximity to the interrogation zone. There is a limit to the maximum size of the lens's numerical aperture due to the geometrical arrangement of the lenses around the interrogation zone 12. By truncating the lenses, they may be located the same distance from the interrogation zone 12 as a spherical lens, while having an increased height and therefore, an increased numerical aperture. With an increased light collecting ability (or increased numerical aperture of the lens surface), the system will be able to provide a brighter image and allow for the visualization of finer details. Preferably, the lenses are truncated to remove the edge of the lens. More preferably, as shown in FIGS. 2 and 3, the lenses are truncated approximately 35% in the horizontal direction to remove both the edge and a portion of the lens within the clear aperture diameter. The lenses may, however, may be truncated by any suitable amount to increase the light collecting ability of the lens system 18, while maintaining a close proximity to the interrogation zone. The width of the lens is the dimension in the plane of FIGS. 1 and 2. The numerical aperture of the lens can be increased by increasing the height of the lens. The power collection efficiency of the lens increases proportionally with the increase in height. The truncated aspherical lenses preferably include a usable numerical aperture of approximately 0.49.

The lens surfaces 20 may include coatings that function to convert the lens surfaces 20 to wavelength specific filters. The coatings may include various inorganic or organic compounds such that the compounds absorb specific wavelengths of light while transmitting other wavelengths. Each lens preferably has a different coating, such that it will filter a specific wavelength that is different from the wavelengths filtered by the other lens surfaces 20. Alternatively at least two lens surfaces 20 may have the same coating. The coated lens surfaces 20 may work cooperatively with the local filters 26 coupled to the detectors 24 that filter specific wavelengths, or may independently filter specific wavelengths.

The detector system of the preferred embodiment functions to detect light from the lens system 18. The detector system preferably includes multiple detectors 24. The detectors are preferably a photomultiplier tube ("PMT") or a photodiode, but may alternatively include any suitable device, such as a camera, to detect light or other electromagnetic energy. In the preferred embodiment, the detector system includes a detector 24 for every lens surface 20 of the lens system 18. The detectors 24 are preferably arranged in a direct path from the lens surfaces 20, and the light collected and directed by the lens system 18 is preferably guided to the detectors 24 by an appropriate light path. The light path is preferably an air channel for simplicity, but may alternatively be a fiber optic cable or any other appropriate waveguide.

The detectors 24 of the preferred embodiment are each coupled to a local filter 26 that independently filters for specific wavelengths. The local filter 26 is preferably easily accessed by the user, such that the user may swap in different filter and change the wavelength detection of the detector system. The step of filtering the light of the first channel preferably does not affect the light of the second channel of the detector system. Thus, the user may easily swap the filters in any order to achieve the same detection parameters. Further, since the each of the detectors is independently aligned with the local filter and the lens surface, the optic system experiences increased reliability and the ruggedness over conventional flow cytometers.

2. The Arrangement of the Lens and Detector Systems

Figure 4:
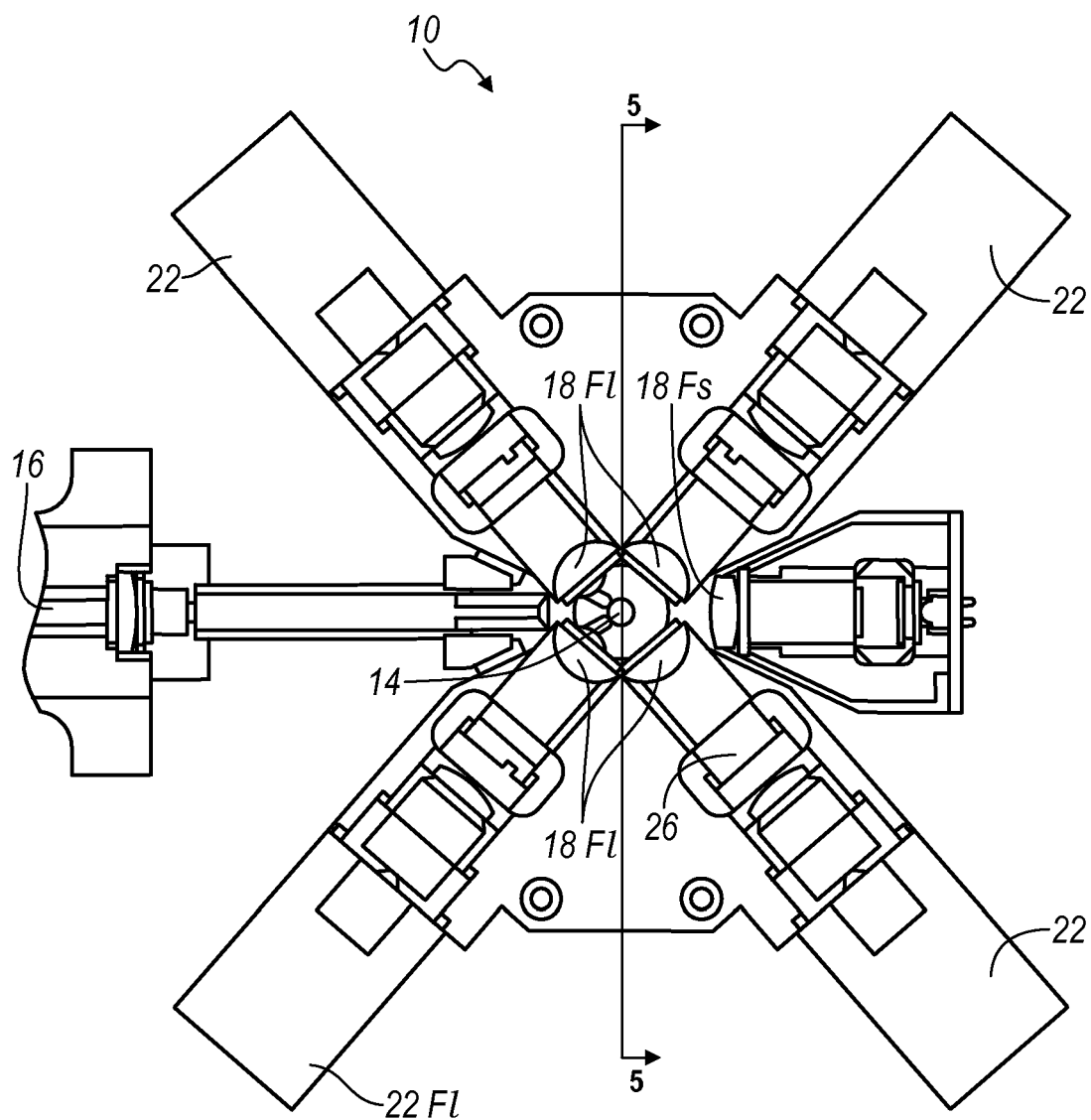
FIGS. 4 and 5 are horizontal and vertical cross sections, respectively, of a first variation of the lens and detector system arrangement of the preferred embodiment.
Figure 5:
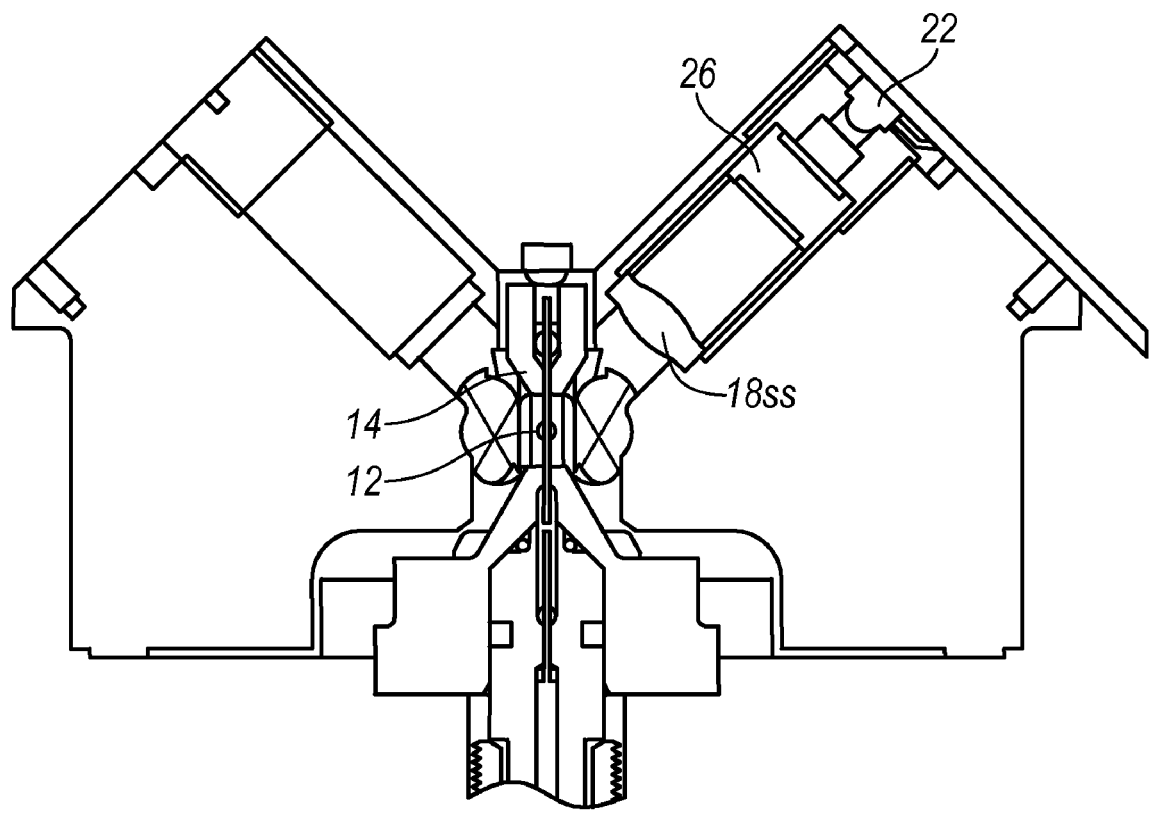

As shown in FIGS. 1 and 4-6, the lens system 18 preferably includes at least two lenses 18ss that function to collect side scatter from the interrogation zone of the flow channel, at least two lenses 18fl that function to collect fluorescence from the interrogation zone of the flow channel, and one lens 18fs that functions to collect forward scatter from the interrogation zone of the flow channel. In a first version, as shown in FIG. 1, all of the lenses are arranged in a common plane. In a second version, as shown in FIGS. 4 and 5, the lenses 18fl and 18fs adapted to collect the fluorescence and forward scatter are arranged in a common plane, while the lenses 18ss adapted to collect the side scatter are arranged in a different plane. By moving at least one of the lenses outside of the plane (and thereby reducing number of lenses in the lens system 18 in the plane perpendicular to the flow channel 14), the lenses may be arranged in a more compact configuration around the flow channel 14, while collecting the same amount of emitted light from the interrogation zone 12 as a lens system 18 with more lenses in the same plane. This arrangement provides a more compact lens system 18 and detector system and therefore a smaller flow cytometer system. The lenses 18ss adapted to collect the side scatter may be placed above, below, or both above and below the common plane of the other lenses. These lenses are preferably angled 45 degrees to the common plane of the other lenses, but may alternatively define any other suitable angle. The lenses placed above (and/or alternatively below) the plane are preferably side scatter detectors, but may alternatively detect any suitable light from the interrogation zone. The additional lenses above the plane perpendicular to the flow channel 14, are preferably aligned such that their arrangement is rotated along the axis of the flow channel 14 relative to the arrangement of the lenses in the parallel plane perpendicular to the flow channel 14. The rotation is preferably rotated 45 degrees relative to the arrangement of the parallel plane perpendicular to the flow channel. This arrangement not only creates a more compact lens system 18, but also detects more light in a compact lens system and thus create a more efficient and compact flow cytometer.

Figure 6:
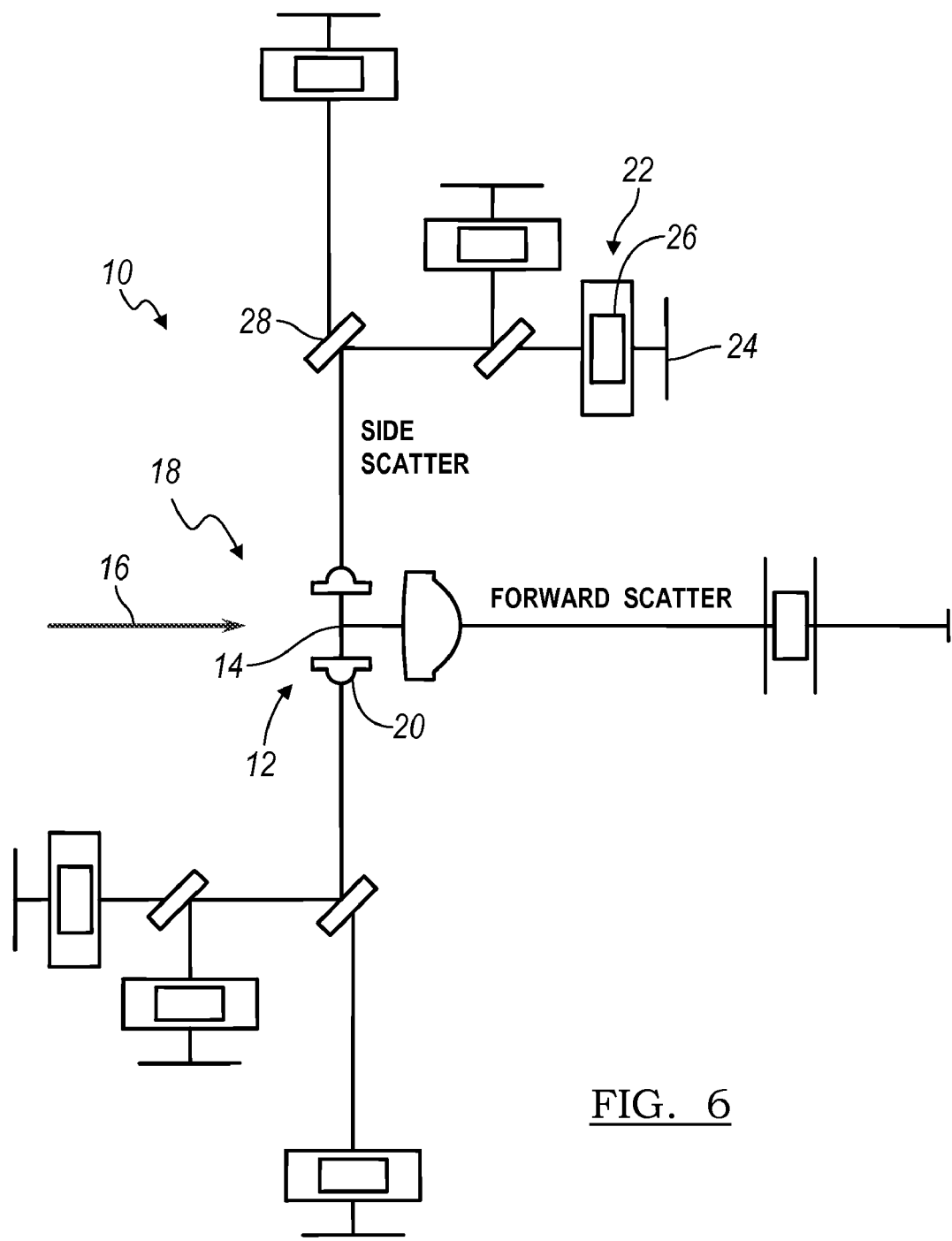
FIG. 6 is a schematic representation of a second variation of the lens and detector system arrangement of the preferred embodiment.

In a second variation of the preferred embodiment, as shown in FIG. 6, the detector system includes more detectors 24 than lens surfaces 20 of the lens system 18. In this variation, the lens system 18 also includes conventional optic devices, such as beam splitters 28, to branch the collected and directed light to the detector system. In this variation, the beam splitters 28 are preferably nonselective with regard to wavelength, which preserves the freedom to independently filter for specific wavelengths (by using local filters 26) at each of the various detectors 24.

3. Ambient Light Absorption for the Detectors

Figure 7:
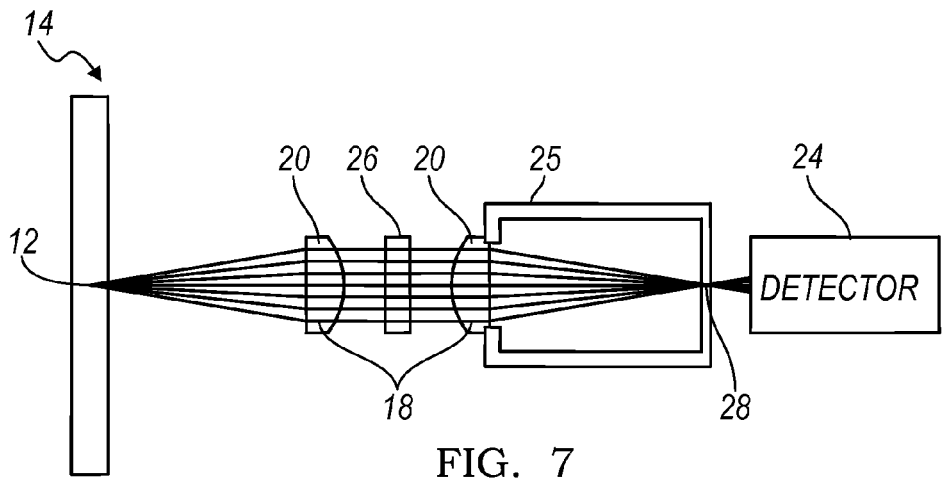
FIG. 7 is a schematic representation of the ambient light absorption of the detectors of the preferred embodiment.

As shown in FIG. 7, the some of the detectors of the preferred embodiment (such as the fluorescence detectors and, additionally or alternatively, the side scatter detectors) include at least one collimating lens 18, a local filter 26, an absorption element 25, and a detector 24 to detect light emitted from the interrogation zone 12 of a flow channel 14. The collimating lens 18 functions to collimate the light received from an interrogation zone 12 on a flow channel 14. The collimated light is then filtered by the local filter 26, and preferably decollimated by another collimating lens 18, before passing through the absorption element 25. The local filter 26 functions to filter the light by allowing certain wavelengths of light to pass through. The local filter 26 preferably absorbs the light at blocked wavelengths, however, it may reflect the blocked wavelengths of light back through the interrogation zone 12 on a flow channel 14 and into another detector system perfectly aligned with the current detector system. The absorption element 25 functions to trap and absorb any light and/or ambient that is not in the focused beam. Preferably, at one end of the absorption element 25 is a collimating lens that accepts collimated light and focuses the collimated light. More preferably, at the other end of the absorption element 25 is a hole 28 to allow the focused beam of light to pass through to a detector 24. The absorption element 25 is preferably shaped as a canister, with a large opening for a collimated lens 18 to focus collimated light and a small opening 28 for the light focused by the collimated lens 18 to exit the absorption element 25 and enter a detector 24. However, the absorption element 25 may be of any shape that allows the absorption element 25 to trap light as desired. The absorption element 25 is preferably black in color, to absorb light, but may alternatively be any color or material that will allow the absorption element 25 to absorb light. The absorption element 25 is preferably made of plastic, but may alternatively be made from any material that may allow the absorption element 25 to absorb light.

4. Retroreflectance for the Fluorescence Detectors

Figure 8:
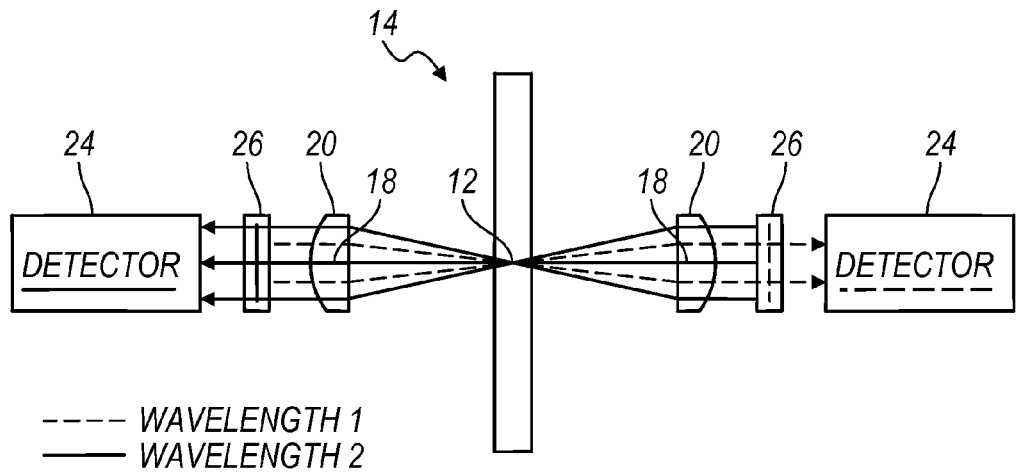
FIG. 8 is a schematic representation of the retroreflectance of the fluorescence detectors of the preferred embodiment.

As shown in FIG. 8, at least two of the fluorescence detectors of the preferred embodiment are located with a particular arrangement and are coupled to a particular local filter 26 such that a first detector absorbs a first wavelength and reflects a second wavelength, while the second detector absorbs the second wavelength and reflects the first wavelength. In a first variation, the two detectors are located on opposite sides of the flow channel 14 and are perfectly aligned such that the light that does not pass through one local filter 26 is reflected, either partially or entirely, back through the lens system 18, and the interrogation zone 12 of the flow channel 14, through the lens system 18, and into the other local filter 26 coupled to the detector 24. The lens coatings 20 on the lenses 18 may also function to reflect and/or filter the light. The lens system 18 is preferably perfectly aligned to have a common focal point between at least two opposing lenses, which may reduce ambient light effects on the collected data. If the opposing detectors 24 are perfectly aligned with each other, the reflected frequencies of light from one local filter 26 will pass through the system and into the corresponding local filter 26 on the other side, and the power of the detected light would significantly increase. While empirical results show that the detected power of light is improved by 40-70%, the detected power of light could theoretically double. In a second variation, three or more detectors may be arranged with appropriate lens such the light that does not pass through one local filter 26 is reflected, either partially or entirely, directly to the lens system 18, and into the other local filter 26 coupled to the detector 24.

By reflecting this light through the interrogation zone 12 of the flow channel 14, it is possible that the sample flowing through the interrogation zone 12 of the flow channel 14 may be re-excited by the reflected light as it travels through the interrogation zone 12 of the flow channel 14. This potential error is preferably minimized or eliminated by appropriate signal processing. Additionally, any reflected light that is detected will have an additional phase delay due to the extra distance traveled by the reflected light. Again, this potential error is preferably minimized or eliminated by appropriate signal processing by using—amongst other information—the distance between the lenses 18 from the center of the flow channel 14 (which is preferably about 6 mm).

While the retroreflectance aspect has been described for the fluorescence detectors, an alternative variation of the preferred embodiment may include the retroreflectance aspect for two or more side scatter detectors.

5. Beam Blocker for the Forward Scatter Detector

Figure 9:
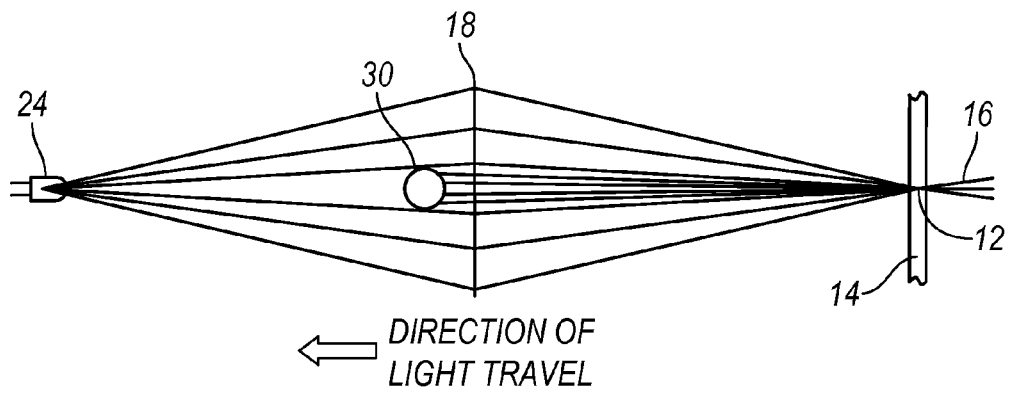
FIG. 9 is a schematic representation of the beam blocker of the forward scatter detector of the preferred embodiment.

As shown in FIG. 9, the forward detector preferably includes a beam blocker 30. The beam blocker 30 functions to reduce or block light from the illumination source (or laser beam) 16 that has passed through the interrogation zone 12 of the flow channel 14 from entering the detectors 24. In a flow cytometer, focused laser light 16 hits the target particles traveling through the interrogation zone 12 capillary 14 and light scatters off the particles in many directions. The focused laser light 16 continues on its previous path as it exits the capillary. The forward scatter detection lens 18 collects specific angles of scattered light (known as forward scatter). This light travels in the same direction as the exiting laser beam 16. The collection lens 18 focuses all the collected light on the detector 24.

The beam blocker 30 is preferably an opaque pin, and is preferably placed between at least one collection lens 18fs and at least one detector 24. The beam blocker 30 is preferably sized specifically to serve as a physical barrier to the laser beam 16 while allowing the scattered light of interest to pass above and below. The scattered light is then preferably recorded by the detector 24 while the beam blocker 30 absorbs and reflects the laser beam 16. The positioning of the beam blocker 30 between the collection lens 18 and the detector 24 takes advantage of the fact that the laser beam 16 is now converging (because of the lens 18fs) to more easily stop the beam 16. The position of the beam blocker 30 also has more tolerance in its position and is preferably not adjustable, enabling cheaper and easier manufacturing and more robust flow cytometer operation.

As a person skilled in the art will recognize from the previous detailed description and from the figures and claims, modifications and changes can be made to the preferred embodiments of the invention without departing from the scope of this invention defined in the following claims.

We claim:

1. An optical system for a flow cytometer that includes a flow channel with an interrogation zone, and an illumination source that impinges the flow channel in the interrogation zone from a particular direction, the optical system comprising:
   a lens system with multiple lens surfaces arranged around the interrogation zone of the flow channel and wherein each lens surface is aimed directly at, and is adapted to collect and collimate light directly from, the interrogation zone; and
   a detection system with multiple detectors adapted to detect light from the lens system, wherein each detector includes a local filter that independently filters for specific wavelengths;
wherein the lens system includes at least one forward scatter lens surface that collects forward scatter from the interrogation zone, at least one side scatter lens surface that collects side scatter from the interrogation zone, and at least one fluorescence lens surface that collects fluorescence from the interrogation zone.

2. The optical system of claim 1, wherein the lens system includes a unitary piece with multiple facets defining the lens surfaces.

3. The optical system of claim 1, wherein the lens system includes multiple lenses.

4. The optical system of claim 3, wherein at least one of the lenses is truncated in the horizontal direction.

5. The optical system of claim 4, wherein the truncated lens is aspherically curved in the vertical direction.

6. The optical system of claim 5, wherein the truncated aspherical lens has a usable numerical aperture value between 0.45 and 0.55.

7. The optical system of claim 3, wherein at least one of the multiple lenses is spherically curved.

8. The optical system of claim 7, wherein the spherical lens has a usable numerical aperture value between 0.25 and 0.35.

9. The optical system of claim 1, wherein at least one of the lens surfaces include a coating adapted to conver the lens surface to a wavelength specific filter.

10. The optical system of claim 1, wherein the detector system includes a detector for each lens surface of the lens system.

11. The optical system of claim 10, wherein the light collected and collimated by the lens surfaces is guided in a direct path to the detectors.

12. The optical system of claim 10, wherein the light collected and collimated by the lens surfaces is guided in an unbranched path to the detectors.

13. An optical system for a flow cytometer that includes a flow channel with an interrogation zone, and an illumination source that impinges the flow channel in the interrogation zone from a particular direction, the optical system comprising:
  a lens system with at least five lens surfaces arranged around the interrogation zone of the flow channel and wherein each lens surface is aimed directly at, and is adapted to collect and collimate light directly from, the interrogation zone; and
  a detection system with multiple detectors adapted to detect light from the lens system, wherein each detector includes a local filter that independently filters for specific wavelengths;
wherein the detector system includes more detectors than lens surfaces of the lens system.

14. The optical system of claim 13, further including at least one beam splitter that branches the collected and collimated light from a lens surface to multiple detectors.

15. The optical system of claim 14, wherein the beam splitter is nonselective with respect to wavelength.

16. The optical system of claim 1, wherein the collimated light from each lens surface passes through an absorption element.

17. The optical system of claim 16, wherein the absorption element includes an aperture.

18. The optical system of claim 17, wherein the absorption element includes a lens surface to focus collimated light through the aperture.

19. The optical system of claim 17, wherein the absorption element includes a canister of absorptive material surrounding the lens surface and defining an aperture centered at the focus of the lens surface.

20. The optical system of claim 1, wherein the local filter coupled to a first detector absorbs a first wavelength and reflects a second wavelength, and the local filter coupled to a second detector absorbs the second wavelength and reflects the first wavelength.

21. The optical system of claim 20, wherein the first detector is located on the opposite side of the interrogation zone from the second detector.

22. The optical system of claim 21, wherein the detectors perform signal processing to remove phase delay on the reflected light.

23. The optical system of claim 20, wherein the first detector and the second detector are aligned such that light reflected from the local filter coupled to the first detector enters the second detector and light reflected from second local filter coupled to the second detector enters the first detector.

24. The optical system of claim 23, wherein the lens surfaces are perfectly aligned to have a common focal point between two opposing lens surfaces.

25. The optical system of claim 1, further comprising a beam blocker between a lens surface and a detector.

26. The optical system of claim 25, wherein the beam blocker is an opaque pin.

27. The optical system of claim 25, wherein the beam blocker position is fixed.

28. The optical system of claim 1, wherein the lens system includes four lens surfaces arranged in a first plane and adapted to collect fluorescence from the interrogation zone of the flow channel.

29. The optical system of claim 28, wherein the first plane is perpendicular to the flow channel, and wherein the lens system includes two lens surfaces arranged outside of the first plane and adapted to collect side scatter from the interrogation zone of the flow channel.

30. The optical system of claim 29, wherein the two lens surfaces arranged outside of the first plane are arranged in a second plane parallel to the first plane, wherein the arrangement of the lens surfaces in the second plane is rotated 45 degrees around the axis of the flow channel, relative to the arrangement of the lens surfaces in the first plane.

31. The optical system of claim 1, wherein each local filter is swappable with another filter.

32. The optical system of claim 1, wherein the detector system includes more detectors than lens surfaces of the lens system.

33. The optical system of claim 1, further including at least one beam splitter that branches the collected and collimated light from a lens surface to multiple detectors.

34. The optical system of claim 13, wherein the lens system includes a unitary piece with multiple facets defining the lens surfaces.

35. The optical system of claim 13, wherein the lens system includes multiple lenses.

36. The optical system of claim 13, wherein the light collected and collimated by the lens surfaces is guided in a direct path to the detectors.

37. The optical system of claim 13, wherein the light collected and collimated by the lens surfaces is guided in an unbranched path to the detectors.

38. The optical system of claim 13, wherein the collimated light from each lens surface passes through an absorption element.

39. The optical system of claim 13, wherein the local filter coupled to a first detector absorbs a first wavelength and reflects a second wavelength, and the local filter coupled to a second detector absorbs the second wavelength and reflects the first wavelength.

40. The optical system of claim 39, wherein the first detector and the second detector are aligned such that light reflected from the local filter coupled to the first detector enters the second detector and light reflected from second local filter coupled to the second detector enters the first detector.

41. The optical system of claim 13, further comprising a beam blocker between a lens surface and a detector.

42. The optical system of claim 13, wherein each local filter is swappable with another filter.

43. The optical system of claim 31, wherein the lens system includes at least two fluorescence lens surfaces that collect fluorescence from the interrogation zone.

* * * * *